(12) United States Patent
Choi et al.

(10) Patent No.: US 9,988,372 B2
(45) Date of Patent: Jun. 5, 2018

(54) CRYSTALLINE FORM OF 5-CHLORO-N-({(5S)-2-OXO-3-[4-(5,6-DIHYDRO-4H-[1,2,4]TRIAZIN-1-YL)PHENYL]-1,3-OXAZOLIDIN-5-YL}METHYL)THIO-PHENE-2-CARBOXAMIDE METHANESULFONATE AND PHARMACEUTICAL COMPOSITION COMPRISING SAME

(71) Applicants: GREEN CROSS CORPORATION, Yongin-si, Gyeonggi-do (KR); LEGOCHEM BIOSCIENCES, INC., Daejeon (KR)

(72) Inventors: Soongyu Choi, Yongin-si (KR); Jungsub Choi, Yongin-si (KR); So-Hyun Yoon, Yongin-si (KR); Yoo Hoon Kim, Yongin-si (KR); Jae Yeon Kim, Yongin-si (KR); Suk Ho Lee, Yongin-si (KR); Young Lag Cho, Daejeon (KR); Ho Young Song, Daejeon (KR); Dae Yon Lee, Daejeon (KR); Sung Yoon Baek, Daejeon (KR); Sang Eun Chae, Daejeon (KR); Tae Kyo Park, Daejeon (KR); Sung Ho Woo, Daejeon (KR); Yong Zu Kim, Daejeon (KR)

(73) Assignees: GREEN CROSS CORPORATION, Yongin-si (KR); LEGOCHEM BIOSCIENCES, INC., Daejeon (KR)

( * ) Notice: Subject to any disclaimer, the term of this patent is extended or adjusted under 35 U.S.C. 154(b) by 0 days. days.

(21) Appl. No.: 15/325,521

(22) PCT Filed: Jul. 18, 2014

(86) PCT No.: PCT/KR2014/006555
§ 371 (c)(1),
(2) Date: Jan. 11, 2017

(87) PCT Pub. No.: WO2016/010178
PCT Pub. Date: Jan. 21, 2016

(65) Prior Publication Data
US 2017/0152251 A1 Jun. 1, 2017

(51) Int. Cl.
| | |
|---|---|
| *C07D 253/065* | (2006.01) |
| *C07D 409/10* | (2006.01) |
| *C07D 413/10* | (2006.01) |
| *A61K 31/53* | (2006.01) |
| *C07D 413/14* | (2006.01) |

(52) U.S. Cl.
CPC ............ *C07D 413/14* (2013.01); *A61K 31/53* (2013.01); *C07D 253/065* (2013.01); *C07D 409/10* (2013.01); *C07B 2200/13* (2013.01)

(58) Field of Classification Search
CPC .............. C07D 253/065; C07D 409/10; C07D 413/10; C07D 413/14; A61K 31/53
USPC .............................. 544/182; 514/242; 549/69
See application file for complete search history.

(56) References Cited

U.S. PATENT DOCUMENTS

| | | | |
|---|---|---|---|
| 8,178,525 | B2 | 5/2012 | Song et al. |
| 8,754,210 | B2 | 6/2014 | Cho et al. |
| 2011/0112083 | A1 | 5/2011 | Song et al. |
| 2012/0136149 | A1 | 5/2012 | Cho et al. |

FOREIGN PATENT DOCUMENTS

| | | |
|---|---|---|
| JP | 2011-526624 A | 10/2011 |
| KR | 10-0898361 B1 | 5/2009 |
| KR | 10-2011-0004590 A | 1/2011 |
| WO | 2011/005029 A2 | 1/2011 |

OTHER PUBLICATIONS

International Searching Authority, International Search Report of PCT/KR2014/006555, dated Apr. 15, 2015. [PCT/ISA/210].
Kazuhide Ashizawa et al., "Crystalline Polymorphism and Crystallizing Science in Pharmaceuticals—Trend of Development/Production and Regulation", Maruzen PLA-NET Corporation, Sep. 20, 2002, 2002, pp. 3-16. (18 pages total).
Pharmacy study-foundation, application, Nanzando Co Ltd, pp. 142-145 (7 pages total).
New tablet study, Nanzando Co Ltd, Apr. 25, 1984, pp. 102-103, 232-233. (7 pages total).
New and pharmaceutics Outline (3rd edition of revision), Apr. 10, 1987, Nankodo Co Ltd, p. 111. (4 pages total).
Experimental science lecture 2 Separation, refining, Maruzen Co Ltd, Jan. 25, 1967, pp. 159-178, 186-187. (25 pages total).
Chong-Hui Gu et al., "Grouping solvents by statistical analysis of solvent property parameters: implication to polymorph screening", International Journal of Pharmaceutics, vol. 283, 2004, pp. 117-125. (10 pages total).
Japanese Patent Office, Communication dated Jan. 23, 2018 in counterpart application No. 2017-523744.

*Primary Examiner* — Venkataraman Balasubramanian
(74) *Attorney, Agent, or Firm* — Sughrue Mion, PLLC

(57) ABSTRACT

The present invention relates to a novel crystalline form of 5-chloro-N-({(5S)-2-oxo-3-[4-(5,6-dihydro-4H-[1,2,4]triazin-1-yl)phenyl]-1,3-oxazolidin-5-yl}methyl)thiophene-2-carboxamide methanesulfonate and a pharmaceutical composition containing the same. The novel crystalline form of a compound according to the present invention exhibits excellent stability even in high-temperature and humidity environments, and thus can be favorably used to prevent or treat diseases, such as thrombosis, myocardial infarction, atherosclerosis, inflammation, stroke, angina pectoris, restenosis after angioplasty, and thromboembolism.

4 Claims, 8 Drawing Sheets

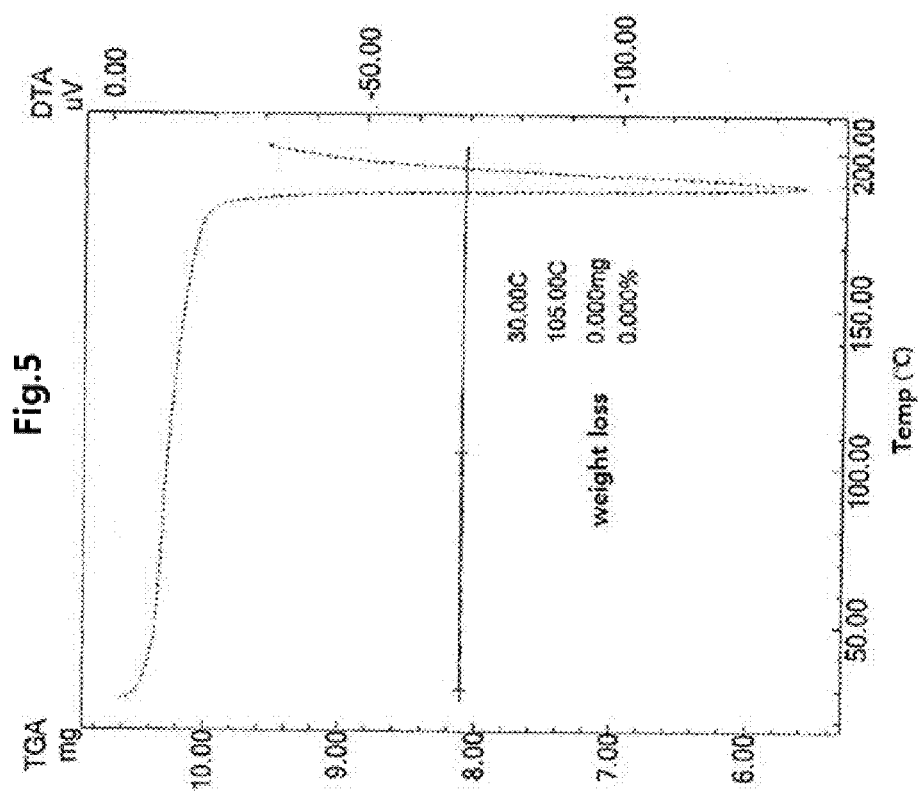

FIG. 6A    (A) Crystalline Form 1
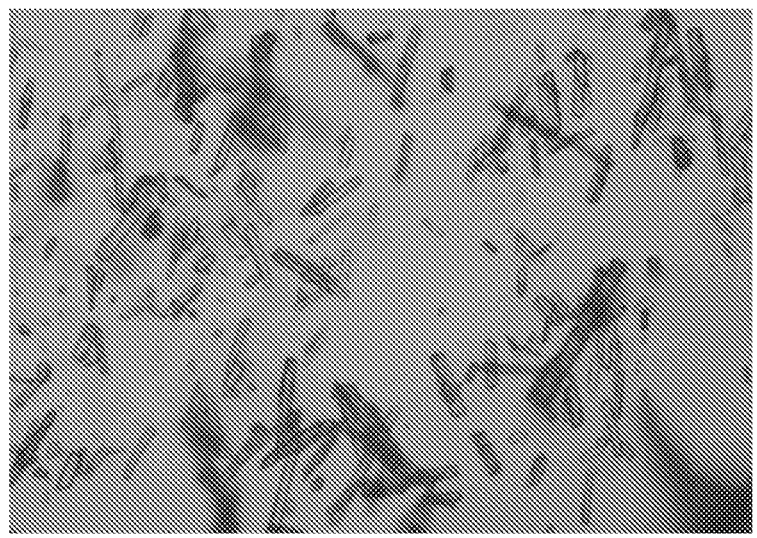
FIG. 6B    (B) Crystalline Form 5
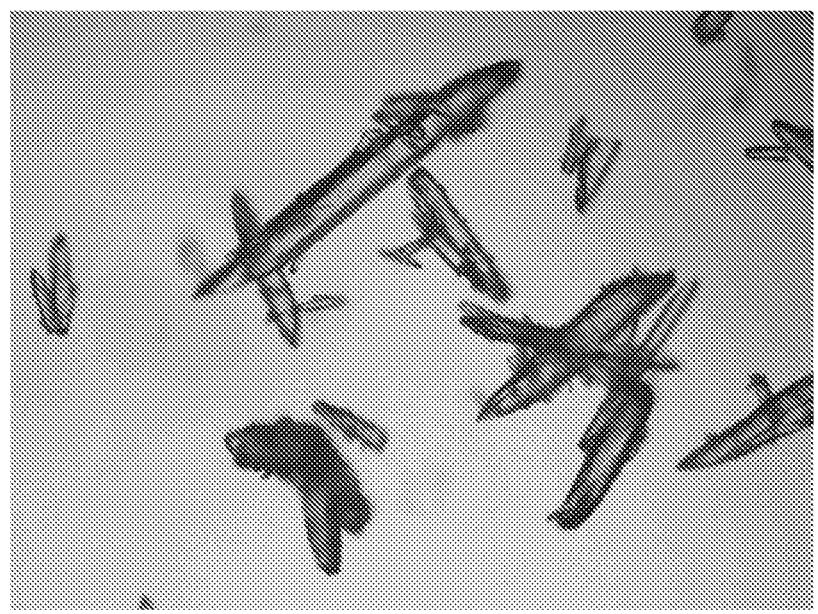

CRYSTALLINE FORM OF 5-CHLORO-N-({(5S)-2-OXO-3-[4-(5,6-DIHYDRO-4H-[1,2,4]TRIAZIN-1-YL)PHENYL]-1,3-OXAZOLIDIN-5-YL}METHYL)THIOPHENE-2-CARBOXAMIDE METHANESULFONATE AND PHARMACEUTICAL COMPOSITION COMPRISING SAME

CROSS REFERENCE TO RELATED APPLICATIONS

This application is a National Stage of International Application No. PCT/KR2014/006555 filed Jul. 18, 2014, the contents of all of which are incorporated herein by reference in their entirety.

TECHNICAL FIELD

The present invention relates to a novel crystalline form of 5-chloro-N-({(5S)-2-oxo-3-[4-(5,6-dihydro-4H-[1,2,4]triazin-1-yl)phenyl]-1,3-oxazolidin-5-yl}methyl)thiophene-2-carboxamide methanesulfonate and a pharmaceutical composition comprising the same.

The present invention has been accomplished under the auspices of National Research and Development Project (Detailed Project No.: KDDF-201210-04; Project Identification No.: 1345193908; Research Project Title: Development of novel therapeutic agent for the inhibition of blood coagulation factor Xa).

BACKGROUND ART

5-Chloro-N-({(5S)-2-oxo-3-[4-(5,6-dihydro-4H-[1,2,4]triazin-1-yl)phenyl]-1,3-oxazolidin-5-yl}methyl)thiophene-2-carboxamide methanesulfonate of the following formula (1) has been known as an inhibitor of blood coagulation factor Xa and used for treating and preventing thrombosis, myocardial infarction, arteriosclerosis, inflammation, stroke, angina pectoris, recurrent stricture after angioplasty, and thromboembolism such as intermittent claudication (see U.S. Pat. No. 8,178,25).

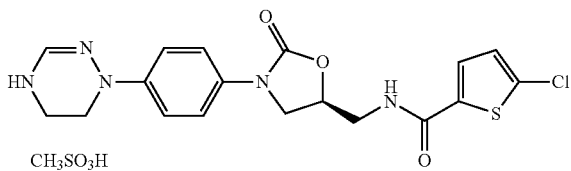

(1)

According to the guidelines and regulations which are promulgated by drug regulatory authorities in various countries, the stability of a drug crystal is required for obtaining the market approval of the drug. Accordingly, there has been a need for developing a novel crystalline form of 5-chloro-N-({(5S)-2-oxo-3-[4-(5,6-dihydro-4H-[1,2,4]triazin-1-yl)phenyl]-1,3-oxazolidin-5-yl}methyl)thiophene-2-carboxamide methanesulfonate which has an excellent dissolution rate and stability even in a high temperature and humid environments.

SUMMARY OF INVENTION

It is an object of the present invention to provide a novel crystalline form of 5-chloro-N-({(5S)-2-oxo-3-[4-(5,6-dihydro-4H-[1,2,4]triazin-1-yl)phenyl]-1,3-oxazolidin-5-yl}methyl)thiophene-2-carboxamide methanesulfonate which is uniform and stable.

It is another object of the present invention to provide a pharmaceutical composition comprising the novel crystalline form for treating or preventing at least one disease or symptom selected from the group consisting of thrombosis, myocardial infarction, arteriosclerosis, inflammation, stroke, angina pectoris, recurrent stricture after angioplasty, and thromboembolism such as intermittent claudication.

In accordance with one aspect of the present invention, there is provided an anhydrous crystalline 5-chloro-N-({(5S)-2-oxo-3-[4-(5,6-dihydro-4H-[1,2,4]triazin-1-yl)phenyl]-1,3-oxazolidin-5-yl}methyl)thiophene-2-carboxamide methanesulfonate, whose X-ray powder diffraction spectrum using Cu-Kα radiation comprises peaks at an angle of diffraction 2θ of 4.302, 8.621, 9.606, 12.103, 12.879, 15.648, 17.353, 17.949, 19.26, 19.577, 20.252, 21.792, 23.108, 23.356, 25.76 and 27.463.

In accordance with another aspect of the present invention, there is provided an anhydrous crystalline 5-chloro-N-({(5S)-2-oxo-3-[4-(5,6-dihydro-4H-[1,2,4]triazin-1-yl)phenyl]-1,3-oxazolidin-5-yl}methyl)thiophene-2-carboxamide methanesulfonate, whose X-ray powder diffraction spectrum using Cu-Kα radiation comprises peaks at an angle of diffraction 2θ of 12.022, 15.721, 15.971, 18.125, 18.928, 19.979, 20.311, 20.726, 21.66, 22.805, 23.18, 23.985, 25.857, 27.25, 27.829, 28, 28.189 and 29.753.

The present invention also provide a pharmaceutical composition comprising the anhydrous crystalline 5-chloro-N-({(5S)-2-oxo-3-[4-(5,6-dihydro-4H-[1,2,4]triazin-1-yl)phenyl]-1,3-oxazolidin-5-yl}methyl)thiophene-2-carboxamide methanesulfonate as an active ingredient.

The inventive novel crystalline compound has an excellent dissolution rate and stability even in a high temperature and humid environments, and, thus, can be effectively used for preventing or treating at least one disease or symptom selected from the group consisting of thrombosis, myocardial infarction, arteriosclerosis, inflammation, stroke, angina pectoris, recurrent stricture after angioplasty, and thromboembolism such as intermittent claudication.

BRIEF DESCRIPTION OF DRAWINGS

The above and other objects and features of the present invention will become apparent from the following description of the invention, when taken in conjunction with the accompanying drawings, which respectively show:

FIG. 5 shows results of thermogravimetric analysis of Crystalline Form 5.

FIGS. 6(A) and 6(B) are photographs of polarized microscope of Crystalline Forms 1 and 5, respectively.

BEST MODE FOR CARRYING OUT THE INVENTION

Figure 1:
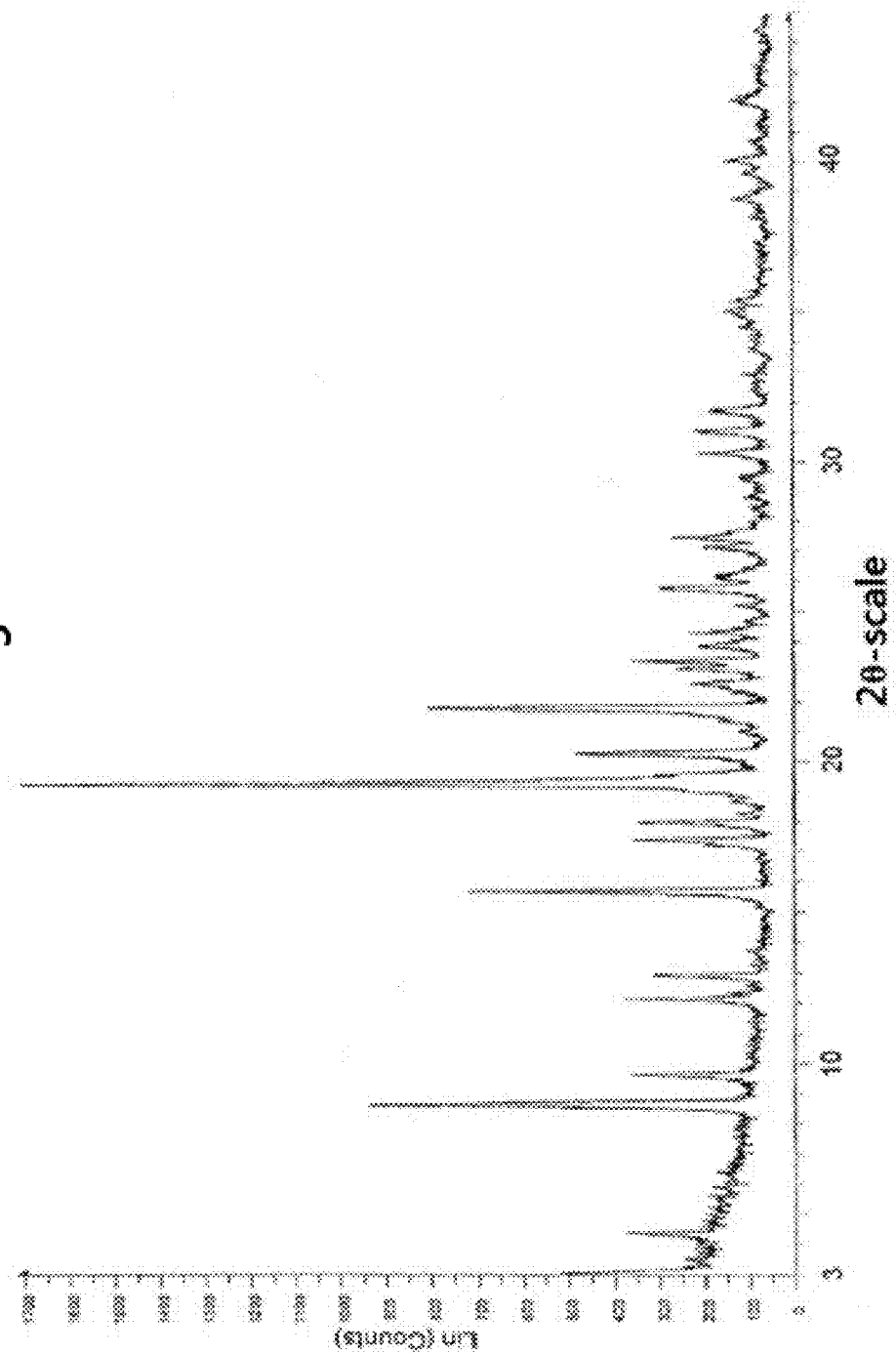
FIG. 1 shows analysis results of X-ray powder diffraction (PXRD) of Crystalline Form 1.

Hereinafter, the present invention is described more specifically.

The novel crystalline form of 5-chloro-N-({(5S)-2-oxo-3-[4-(5,6-dihydro-4H-[1,2,4]triazin-1-yl)phenyl]-1,3-oxazolidin-5-yl}methyl)thiophene-2-carboxamide methanesulfonate (hereinafter referred to as "GCC-4401C") according to the present invention has an excellent solubility and stability in a high temperature and humid environments.

The novel crystalline form of GCC-4401C can be easily obtained by a crystallization method by organic solvent cooling, a vacuum crystallization method or a solvent-antisolvent crystallization method.

GCC-4401C which is used as a reaction material can be prepared by the method disclosed in WO2011/005029. The novel crystalline compound according to the present invention can be prepared by dissolving the reaction material in an organic solvent, adding an anti-solvent thereto and cooling the mixture, followed by filtering and drying the crystals formed therein.

The organic solvents that may be used are selected from the group consisting of methanol, dimethylacetamide (DMA), dimethylsulfoxide (DMSO) and combinations thereof, and methanol is preferred. The anti-solvents that may be used are selected from the group consisting of isopropyl alcohol (IPA), n-butanol, ethyl acetate, toluene and combinations thereof, and n-butanol is preferred.

The anti-solvent can be used in an amount of 1 to 10 folds by volume, preferably 2 to 3 folds by volume, based on the volume of the organic solvent.

The crystals, formed by the addition of an anti-solvent and cooling of the mixture, can be filtered out by a conventional filtration method, and then dried at the temperature ranging from 55 to 65° C. for 3 to 4 hours for removing the residual solvent to obtain the novel crystalline compound of the present invention.

According to one embodiment of the present invention, the novel crystalline compound referred to as Crystalline Form 1 can be obtained from the process in which GCC-4401C is dissolved in an organic solvent (e.g., methanol), an anti-solvent (e.g., n-butanol) is added thereto and the mixture is cooled, and then the crystals formed in the previous step are filtered and dried at 60±5° C. for 3 to 4 hours.

According to another embodiment of the present invention, the novel crystalline compound referred to as Crystalline Form 5 can be obtained from the process in which GCC-4401C is dissolved in an organic solvent (e.g., methanol), the resulting solution is heated to a temperature of 45° C. or higher, an anti-solvent (e.g., n-butanol) is added thereto and the mixture is cooled, and then the crystals formed in the previous step are filtered and dried at 60±5° C. for 3 to 4 hours.

In accordance with one aspect of the present invention, Crystalline Form 1 has a crystalline structure whose X-ray powder diffraction spectrum using Cu-Kα radiation comprises characteristic peaks at an angle of diffraction 2θ of 4.302, 8.621, 9.606, 12.103, 12.879, 15.648, 17.353, 17.949, 19.26, 19.577, 20.252, 21.792, 23.108, 23.356, 25.76 and 27.463. Each peak at the angle of diffraction 2θ has a relative intensity of 10% or higher. In addition, its differential scanning calorimetry (DSC) analysis shows a peak at 178±2° C. (see Example 1).

In accordance with another aspect of the present invention, Crystalline Form 5 has a crystalline structure whose X-ray powder diffraction spectrum using Cu-Kα radiation comprises characteristic peaks at an angle of diffraction 2θ of 12.022, 15.721, 15.971, 18.125, 18.928, 19.979, 20.311, 20.726, 21.66, 22.805, 23.18, 23.985, 25.857, 27.25, 27.829, 28, 28.189 and 29.753. Each peak at the angle of diffraction 2θ has a relative intensity of 10% or higher. In addition, its differential scanning calorimetry analysis shows a peak at 186±2° C. (see Example 2).

As confirmed from the results of X-ray powder diffraction spectrum, Crystalline Forms 1 and 5 according to the present invention are anhydrous crystalline forms, and have stability without change of crystalline forms even when being ground or exposed to humid conditions (see Test Example 1). Furthermore, the crystalline forms according to the present invention show an excellent dissolution rate of 80% or higher within 10 minutes regardless of the form of the pharmaceutical formulations such as tablets and capsules containing the crystalline forms (see Test Example 2). Thus, the novel crystalline forms of the present invention, Crystalline Forms 1 and 5 of GCC-4401C, are effective for treating thrombosis, myocardial infarction, arteriosclerosis, inflammation, stroke, angina pectoris, recurrent stricture after angioplasty, and thromboembolism such as intermittent claudication.

In accordance with another aspect, the present invention provides a pharmaceutical composition comprising a novel crystalline form of 5-chloro-N-({(5S)-2-oxo-3-[4-(5,6-dihydro-4H-[1,2,4]triazin-1-yl)phenyl]-1,3-oxazolidin-5-yl}methyl)thiophene-2-carboxamide methanesulfonate as an active ingredient.

The pharmaceutical composition of the present invention can further comprise a pharmaceutically acceptable carrier or excipient. The pharmaceutically acceptable carrier, excipient, or combinations thereof can be selected depending on the administration method used for treating a specific patient, types of medical conditions, or disease conditions.

Examples of the pharmaceutically acceptable carrier or excipient are as follows: excipients such as starches, sugar, lactose, dextrin, mannitol, sorbitol, crystalline cellulose, low-substituted hydroxypropyl cellulose, sodium carboxymethyl cellulose, Arabic gum, amylopectin, light anhydrous silicic acid, and synthetic aluminum silicate; fillers or extending agents such as calcium phosphate and silica derivatives; binding agents such as starches, sugar, mannitol, trehalose, dextrin, amylopectin, sucrose, gluten, Arabic gum, methyl cellulose, carboxymethyl cellulose, sodium carboxymethyl cellulose, crystalline cellulose, cellulose derivatives (e.g., including hydroxypropyl cellulose and hydroxypropylmethyl cellulose), gelatin, arginic acid salt, and polyvinyl pyrrolidone; lubricating agents such as talc, magnesium or calcium stearate, hydrogenated castor oil, talcum powder, and solid polyethylene glycol; disintegrants such as povidone, sodium croscarmellose, and crospovidone; and surfactants such as polysorbate, cetyl alcohol and glycerol monostearate.

The pharmaceutical composition of the present invention may be prepared in accordance with any of the conventional procedures. Regarding the conventional formulation procedures, see [*Remington: The Science and Practice of Pharmacy*, 20th Edition, Lippincott Williams & White, Baltimore, Md. (2000)]; and [H. C. Ansel et al., *Pharmaceutical Dosage Forms and Drug Delivery Systems*, 7th Edition, Lippincott Williams & White, Baltimore, Md. (1999)].

The pharmaceutical composition according to the present invention may comprise Crystalline Form 1 or 5 of 5-chloro-N-({(5S)-2-oxo-3-[4-(5,6-dihydro-4H-[1,2,4]triazin-1-yl)phenyl]-1,3-oxazolidin-5-yl}methyl)thiophene-2-carboxamide methanesulfonate as an active ingredient in an amount of 0.1 to 95 wt %, preferably 1 to 70 wt %, based on the total weight of the composition.

The pharmaceutical composition of the present invention may be formulated as an oral or parenteral preparation, etc. and administered to a patient via suitable administration routes. Preferably, the inventive composition may be formulated as capsules, tablets, dispersions, suspensions, etc. and then administered orally.

The pharmaceutical composition according to the present invention can be administered in a single dose or in divided doses per one day, and a typical daily dose for human may range from 2.5 to 80 mg based on the amount of the active ingredient, Crystalline Form 1 or 5 of 5-chloro-N-({(5S)-2-oxo-3-[4-(5,6-dihydro-4H-[1,2,4]triazin-1-yl)phenyl]-1,3-oxazolidin-5-yl}methyl)thiophene-2-carboxamide methanesulfonate.

MODE FOR THE INVENTION

Hereinafter, the present invention is explained in detail by Examples. The following Examples are intended to further illustrate the present invention without limiting its scope.

EXAMPLE

The analysis data described in the following Examples were measured under the following conditions.

1) X-ray powder diffraction (PXRD) spectrum was obtained by X-ray diffraction spectrometer (Bruker Corporation, Germany) using Cu-Kα radiation. The instruments and conditions used for the measurement of PXRD spectum are listed in Table 1 below.

TABLE 1

| Model name and Detector | |
| --- | --- |
| Model name | Bruker Axs, D8 Advance |
| Detector | PSD-Lynx Eye |
| Instrument Setting | |
| Goniometer | Theta/Theta Vertical |
| Mode of collection | Reflection |
| Measuring circle | 435 mm |
| Radiation | Cu Kα (wavelength = 1.5418 Å) |
| Scan Parameters | |
| Voltage (kV) and current (mA) | 40/40 |
| Scan range | 3-45° |
| Step size | 0.013° |
| Time/Step (s) | 0.1 second |
| Operation time (min) | 5:43 |
| Mode of Scan | Continuous |
| Divergent slit | Fixed at 0.1° |
| Anti-scattering slit | 8.0 mm |
| Rotation/min | ON |

2) Differential scanning calorimetry (DSC) was performed by using differential scanning calorimeter (TA Instruments Q2000) at about 50 mL/min under an inert nitrogen atmosphere. Temperature was set at 30° C. to 220° C., and then increased 10° C. per minute.

3) TGA was performed by using Shimadzu DTG-60 at about 30 mL/min under an inert nitrogen atmosphere. Temperature was set at room temperature to 220° C. with a ramp speed of 10° C. /min, and the result were integrated in the range from 30° C. to 105° C.

Example 1

Preparation of Crystalline Form 1 n-Butanol was charged in an automated polyblock reactor (POLYBLOCK 8-station (parallel reactor) Maker: HEL) at room temperature (30±5° C.). 15 g of 5-chloro-N-({(5S)-2-oxo-3-[4-(5,6-dihydro-4H-[1,2,4]triazin-1-yl)phenyl]-1,3-oxazolidin-5-yl}methyl)thiophene-2-carboxamide methanesulfonate (purity: 99.7%) prepared according to the process described in pages 28 to 35 of WO2011/005029 was dissolved in methanol of 8 folds by volume. The resulting solution was added slowly into the reactor. n-Butanol was used in an amount of 20-folds by volume.

The reactant was stirred at room temperature (30±5° C.) for 1 hour, and then cooled slowly to a temperature of 0±5° C. at a rate of 0.5° C./min. The resultant was stirred at the same temperature for 3 hours, and filtered. The filtered material was collected and dried at 60±5 ° C. for 3-4 hours to obtain 10.5 g (99.7%) of a white crystal. The obtained crystal was photographed by polarized microscope (Nikon). FIGS. 6(A) and 6(B) are photographs of polarized microscope of the obtained crystal.

The X-ray powder diffraction (PXRD) spectrum of the crystal thus obtained shows the angles of diffraction (2θ), the interplanar distances (d value) and relative intensities (%) of peaks, as shown in FIG. 1 and Table 2 below. The crystalline compound having these characteristic angles of diffraction (2θ) with a relative intensity of 10% or higher was designated as "Crystalline Form 1."

TABLE 2

| 2θ value (°) | d value | Relative intensity (%) |
| --- | --- | --- |
| 4.302 | 20.5213 | 12.1 |
| 8.621 | 10.24837 | 50.2 |
| 9.606 | 9.20027 | 16.5 |
| 12.103 | 7.30705 | 16.8 |
| 12.879 | 6.86844 | 14.6 |
| 15.648 | 5.6584 | 37.3 |
| 17.353 | 5.10632 | 17.5 |
| 17.949 | 4.93802 | 16.9 |
| 19.26 | 4.60471 | 100 |
| 19.577 | 4.5308 | 12.6 |
| 20.252 | 4.38143 | 25.6 |
| 21.792 | 4.07503 | 45.4 |
| 23.108 | 3.84582 | 10.8 |
| 23.356 | 3.80558 | 15.2 |
| 25.76 | 3.45563 | 13.8 |
| 27.463 | 3.24512 | 11.3 |

Figure 2:
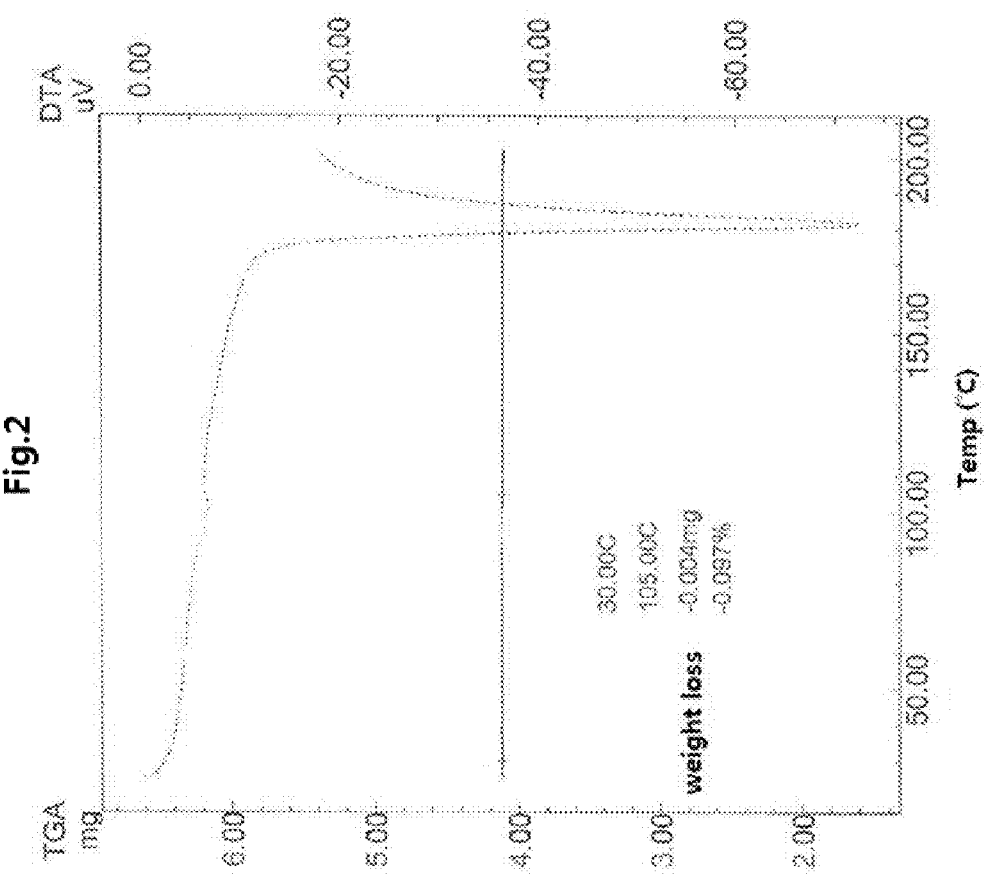
FIG. 2 shows results of thermogravimetric analysis (TGA) of Crystalline Form 1.

The DSC peak, weight loss through TGA, IR spectra and $^{13}$C NMR data of the crystal are listed below. FIG. 2 shows results of TGA of Crystalline Form 1.

DSC peak: 179.33° C.

Weight loss through TGA: 0.09% (w/w)

IR (KBr, cm$^{-1}$): 3301, 3453, 3066, 2939, 2357, 2124, 2018, 1962, 1742, 1670, 1644, 1552, 1509, 1486, 1429, 1411, 1361, 1344, 1323, 1301, 1287, 1217, 1196, 1160, 1146, 1105, 1085, 1032, 991, 930, 882, 839, 821, 803, 776, 751, 729, 707, 683, 667.

$^{13}$C NMR: 160.81, 154.16, 148.00, 143.43, 138.47, 134.06, 133.25, 128.45, 128.18, 119.35, 118.08, 71.32, 47.53, 45.94, 42.17, 40.13, 35.71.

Example 2

Preparation of Crystalline Form 5

Methanol was charged in an automated polyblock reactor (POLYBLOCK 8-station (parallel reactor) Maker: HEL) at room temperature (30±5° C.). 20 g of 5-chloro-N-({(5S)-2-oxo-3-[4-(5,6-dihydro-4H-[1,2,4]triazin-1-yl)phenyl]-1,3-oxazolidin-5-yl}methyl)thiophene-2-carboxamide methanesulfonate (purity: 99.7%) prepared according to the process described in pages 28 to 35 of WO2011/005029 was added into the reactor. The reactant was heated at 45±2° C. to obtain a clear solution.

n-Butanol was added slowly to the solution thus obtained in an amount of 20 folds by volume. The resultant was stirred at the same temperature for 4 to 6 hours, and filtered at the same temperature. The collected product was dried at 60±5° C. for 3 to 4 hours to obtain 15 g (99.7%) of a white crystal. The obtained crystal was photographed by polarized microscope (Nikon). FIGS. 6(A) and 6(B) are photographs of polarized microscope of the obtained crystal.

Figure 3:
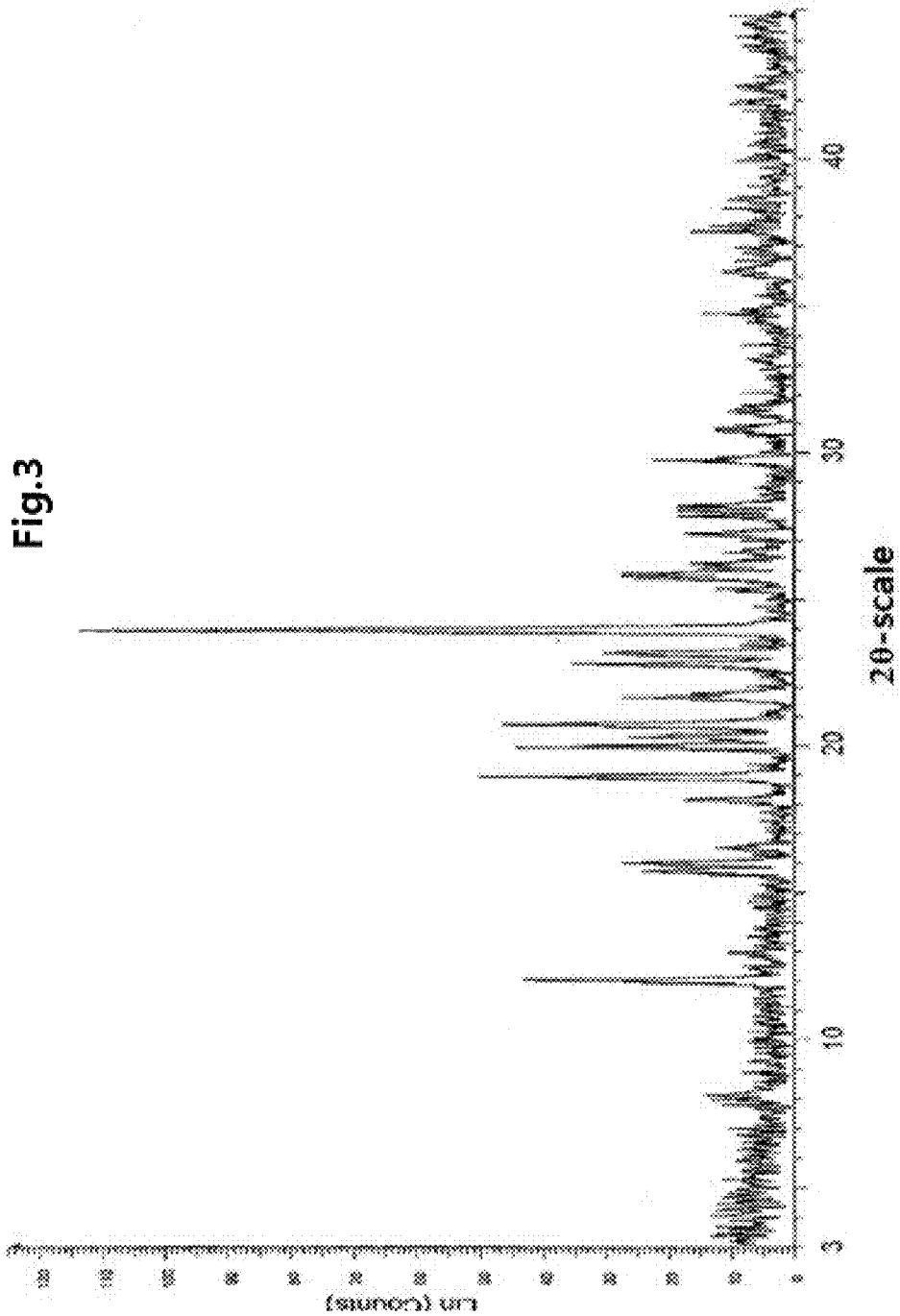
FIG. 3 shows analysis results of X-ray powder diffraction of Crystalline Form 5.

The X-ray powder diffraction (PXRD) spectrum of the crystal thus obtained shows the angles of diffraction (2θ), the interplanar distances (d values) and relative intensities (%) of peaks, as shown in FIG. 3 and Table 3 below. The crystalline compound having these characteristic angles of diffraction (2θ) with a relative intensity of 10% or higher was designated as "Crystalline Form 5."

TABLE 3

| 2θ value (°) | d value | Relative intensity (%) |
|---|---|---|
| 12.022 | 7.35574 | 35 |
| 15.721 | 5.63232 | 19.5 |
| 15.971 | 5.5449 | 20.5 |
| 18.125 | 4.89032 | 13.8 |
| 18.928 | 4.68475 | 36.6 |
| 19.979 | 4.44069 | 29.6 |
| 20.311 | 4.36871 | 20.9 |
| 20.726 | 4.28226 | 38.6 |
| 21.66 | 4.0996 | 21 |
| 22.805 | 3.89624 | 24 |
| 23.18 | 3.83411 | 24.4 |
| 23.985 | 3.70722 | 100 |
| 25.857 | 3.44286 | 18.4 |
| 27.25 | 3.26999 | 12.3 |
| 27.829 | 3.20327 | 10.1 |
| 28 | 3.18411 | 10.3 |
| 28.189 | 3.16314 | 12.9 |
| 29.753 | 3.00034 | 15.4 |

Figure 4:
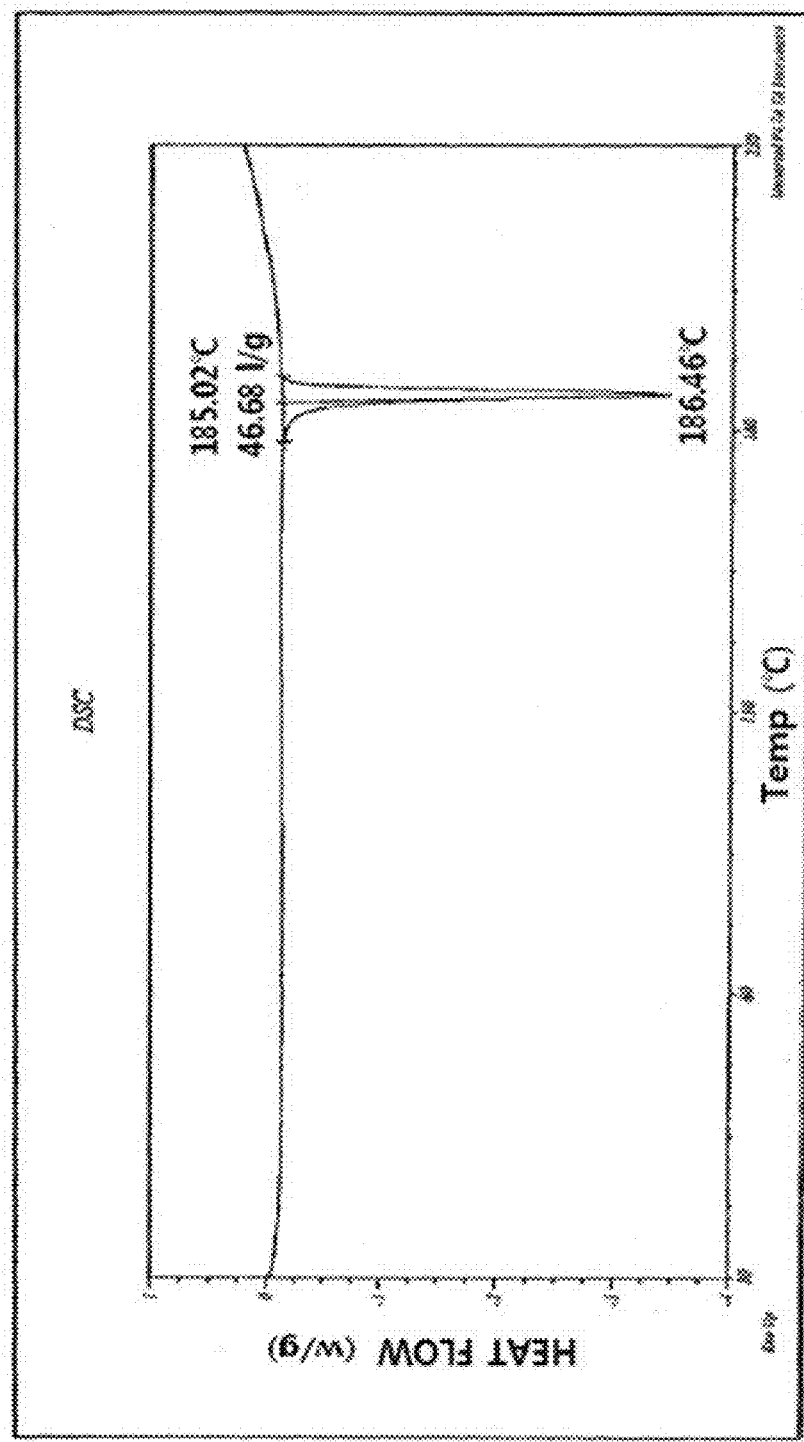
FIG. 4 shows analysis results of differential scanning calorimetry of Crystalline Form 5.

The DSC peak, weight loss through TGA, IR spectra and $^{13}C$ NMR data of the crystal are listed below. FIGS. 4 and 5 show analysis results of DSC and results of TGA of Crystalline Form 5, respectively.

DSC peak: 186° C.
Weight loss through TGA: 0.00% (w/w)
IR (KBr, cm$^{-1}$): 3315, 3236, 3050, 2963, 2439, 2144, 2167, 2135, 2055, 2015, 1892, 1708, 1656, 1572, 1550, 1514, 1479, 1438, 1419, 1429, 1322, 1303, 1273, 1236, 1226, 1202, 1169, 1150, 1082, 1058, 1038, 1018, 996, 943, 882, 821, 807, 777, 757, 723, 685, 671, 655.
$^{13}C$ NMR: 160.81, 154.16, 148.00, 143.43, 138.47, 134.06, 133.25, 128.45, 128.18, 119.35, 118.08, 71.32, 47.53, 45.94, 42.17, 40.13, 35.71.

Test Example 1

Stability of Novel Crystalline Forms

The stability of novel crystalline forms obtained from Examples 1 and 2 was measured according to the following procedures.

1) Measurement of Stability in Solvent Slurry System

In order to determine whether one crystalline form is interconverted into another crystalline form in a stirred solvent, a slurry test was performed in different solvents at room temperature.

First, an automated polyblock reactor was filled with each of the solvents listed in Table 4 below at room temperature (30±5° C.). Crystalline Form 1 was added into the reactor at 30±5° C., and heated and stirred until a transparent solution was obtained. Thereafter, an anti-solvent listed in Table 4 below (n-butanol or IPA) was added into the reactor for 30±15 minutes and stirred for 30±15 minutes until a transparent solution was obtained. The resultant was cooled to a temperature of 0±5° C., stirred for 2-3 hours, and then filtered at 0±5° C. The obtained material was dried at 60±5° C. for 3 to 4 hours in VTD, and then DSC analysis was performed for the obtained sample to identify the final crystalline form.

Another slurry test was performed for Crystalline Form 5 using the solvents listed in Table 4 below in the same manner described above. DSC analysis was performed for the obtained sample to identify the final crystalline form. Table 4 shows the results.

TABLE 4

| Initial form | Solvent system | Solvent (vol) | Anti-solvent (vol) | Final form (DSC peak) |
|---|---|---|---|---|
| Crystalline Form 1 | Acetonitrile | 10 | — | Mixed crystalline forms (179.2, 187.6) |
| | Hexane | 10 | — | Mixed crystalline forms (178.0, 187.0) |
| | Isopropyl alcohol (IPA) | 10 | — | Crystalline Form 5 (187.0) |
| | Methanol: n-butanol | 7 | 20 | Crystalline Form 5 (187.7) |
| | Methanol: IPA | 7 | 20 | Mixed crystalline forms |
| Crystalline Form 5 | Heptane | 10 | — | Crystalline Form 5 (186.44) |
| | Ethyl acetate (EA) | 10 | — | Crystalline Form 5 (186.48) |
| | Methyl tert-butyl ether (MTBE) | 10 | — | Crystalline Form 5 (186.45) |
| | IPA | 10 | — | Crystalline Form 5 (186.33) |
| | Acetonitrile | 10 | — | Crystalline Form 5 (186.88) |
| | n-butanol | 10 | — | Crystalline Form 5 (186.76) |
| | Methanol: n-butanol | 7 | 20 | Crystalline Form 5 (186.27) |
| | Dimethyl acetamide: EA | 3 | 20 | Crystalline Form 5 (187.05) |
| | MeOH: IPA | 7 | 20 | Crystalline Form 5 (186.80) |

As shown in Table 4, Crystalline Form 1 tends to convert into Crystalline Form 5 while it is stirred in the solvent for 24 hours, whereas Crystalline Form 5 maintains the initial form even when it is stirred in various combinations of solvents for 24 hours, which indicates the stability of Crystalline Form 5.

2) Measurement of Interconversion at High Temperature

In order to determine the interconversion of crystalline forms at a high temperature, each of Crystalline Forms 1 and 5 was dried at 80±5° C. in non-vacuum state, and then cooled to a temperature of 30±5° C. DSC analysis was performed for the obtained samples to identify the final crystalline form. Table 5 shows the results.

TABLE 5

| Initial form (DSC peak) | Final form (DSC peak) |
|---|---|
| Crystalline Form 1 (178.0) | Crystalline Form 1 (178.0) |
| Crystalline Form 5 (186.0) | Crystalline Form 5 (187.0) |

As shown in Table 5, it is confirmed that Crystalline Forms 1 and 5 according to the present invention are stable at high temperature.

3) Measurement of Stability Under Physical Stimulus

Multi-milling, manual grinding and humidification test were performed for the crystalline forms of the present invention to confirm their stability under physical stimulus. For multi-milling test, each of Crystalline Forms 1 and 5 was milled at 3,000 rpm by using a prototype multi-mill instrument (Sreenex Machines Pvt. Ltd.). For manual grinding, each of the crystalline forms was gradually ground by using a pestle and mortar. In the humidification test, Crystalline Forms 1 and 5 were stored at 30° C. and 90% RH for 24 hours.

DSC analysis was performed for the crystalline forms obtained from the tests to identify the final crystalline form. Table 6 shows the results.

TABLE 6

|  | Crystalline Form 1 | | Crystalline Form 5 | |
|---|---|---|---|---|
|  | Initial form | Final form | Initial form | Final form |
| Multi-milling | Crystalline Form 1 | Crystalline Form 1 | Crystalline Form 5 | Crystalline Form 5 |
| Manual grinding | Crystalline Form 1 | Crystalline Form 1 | Crystalline Form 5 | Crystalline Form 5 |
| Humidification | Crystalline Form 1 | Crystalline Form 1 | Crystalline Form 5 | Crystalline Form 5 |

As shown in Table 6, it is confirmed that both Crystalline Forms 1 and 5 of the present invention are stable under physical stimulus such as milling, grinding and humidification.

4) Solubility

The solubility of each of Crystalline Forms 1 and 5 of the present invention was measured after being dissolved in the methanol solvent. As a result, the solubility of Crystalline Form 1 was 70 mg/mL, while the solubility of Crystalline Form 5 was 30 mg/mL, which indicates that Crystalline Form 5 is more stable than Crystalline Form 1.

Test Example 2

Dissolution Test of Novel Crystalline Forms

1) Preparation of Capsules

Capsules containing Crystalline Form 1 of the present invention were prepared according to a conventional capsulation method. First, 20 mg of Crystalline Form 1 of the present invention and 279.1 mg of lactose were added into a V-Mixer, which is generally used in the mixing procedure for manufacturing medicines, and then mixed at 20 rpm for 20 minutes. 0.9 mg of magnesium stearate was added thereto, and the mixture was further mixed at 20 rpm for 5 minutes. The mixture was filled into hard gelatin capsules to prepare capsules of Crystalline Form 1.

2) Preparation of Tablets

Tablets containing Crystalline Form 1 or 5 of the present invention were prepared according to a conventional tableting method.

Specifically, 20 mg of Crystalline Form 1, 175.5 mg of lactose, 7 mg of Primojel, 5 mg of hydroxypropylmethyl cellulose (HPMC) and 1.5 mg of Aerosil 200 were added into a V-Mixer, which is generally used in the mixing procedure for manufacturing medicines, and then mixed at 20 rpm for 20 minutes. 1 mg of magnesium stearate was added thereto, and the mixture was further mixed at 20 rpm for 5 minutes. The mixture was compressed into tablets by using a tablet press. Film-coated tablets containing Crystalline Form 1 prepared by coating the obtained tablets with about 10 mg of Opadry.

The above procedures were repeated except that Crystalline Form 5 was used instead of Crystalline Form 1 to prepare film-coated tablets containing Crystalline Form 5.

3) Dissolution Test

Dissolution test was performed for the capsules and tablets prepared above to measure the dissolution rate (%) thereof.

Dissolution test was performed according to Paddle method of U.S.P. Apparatus 2 at a paddle speed of 50 rpm. Acetate buffer, pH 4.0 was used as a dissolution solution, and the capsules or tablets were added when 900 mL of dissolution solution reached 37±0.5° C. At the predetermined time (5 minutes, 10 minutes, 15 minutes and 30 minutes), 1 mL of each sample was taken from the dissolved solution and filtered. The dissolution rate was measured by using HPLC. The test was performed once (N=6).

Mean and standard deviation (S.D.) of the dissolution rates are shown in Table 7 below and FIG. 7.

TABLE 7

|  | 5 minutes | | 10 minutes | | 15 minutes | | 30 minutes | |
|---|---|---|---|---|---|---|---|---|
|  | Mean | S.D. | Mean | S.D. | Mean | S.D. | Mean | S.D. |
| Tablets (Crystalline Form 1) | 61.5 | 10.5 | 88.2 | 8.1 | 94.4 | 4.6 | 98.5 | 2.4 |
| Tablets (Crystalline Form 5) | 53.4 | 12.5 | 83.1 | 5.0 | 89.6 | 2.2 | 96.7 | 0.4 |
| Capsules | 49.7 | 5.9 | 87.4 | 6.8 | 97.8 | 3.7 | 100.0 | 4.0 |

Generally, capsules do not require a large amount of excipient and have the advantage of simple manufacturing process. However, capsules have problems with stability since a capsule itself is vulnerable to humidity and the components in the capsule are not compressed, which results in large surface area, thereby being easily influenced by external environment. Tablets can remedy the shortcomings of capsules, and have advantages of excellent production efficiency and the low production cost. Meanwhile, polymorphs have the same constituent unit of a crystal, but different arrangement thereof, and the solubility thereof may be affected depending on the arrangement.

Figure 7:
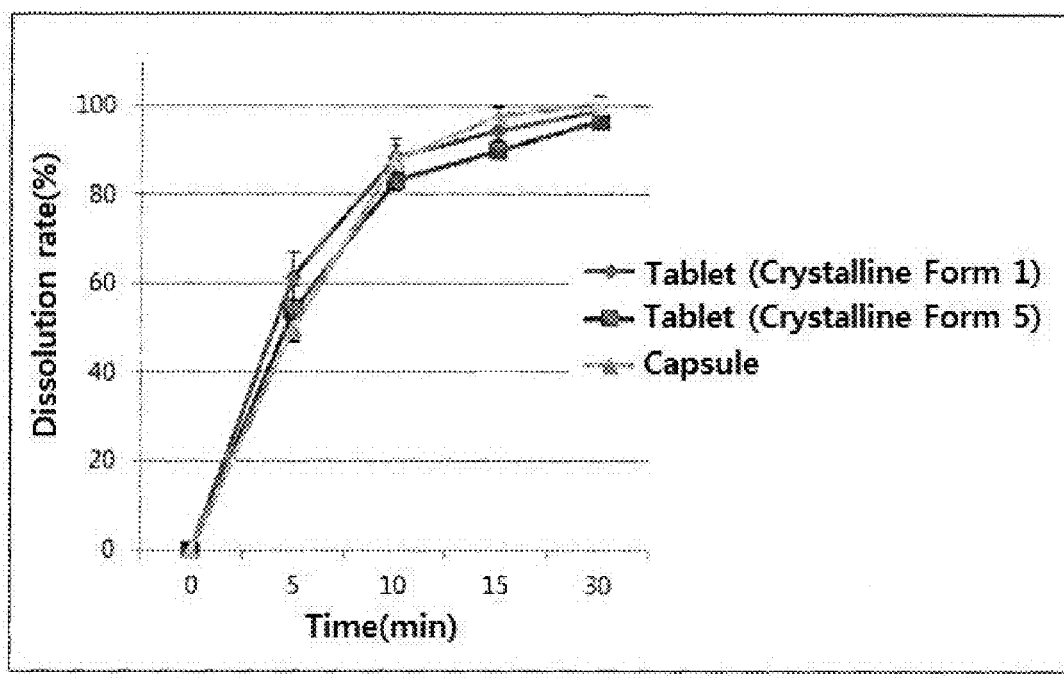
FIG. 7 is a graph comparing the dissolution rates of capsules and tablets containing Crystalline Form 1 or 5 of the present invention.

As shown in Table 7 and FIG. 7, both the tablets and capsules of the present invention have an excellent dissolution rate of 80% or higher within 10 minutes.

Furthermore, the crystalline forms according to the present invention in capsule form show dissolution rates similar to those in tablet form, which confirms the equivalency of solubility between capsules and tablets. Tablets containing Crystalline Form 1 show dissolution pattern similar to those containing Crystalline Form 5, which confirms that Crystalline Forms 1 and 5 of the present invention have similar solubility and pharmacological effects.

4) Dissolution Test in Mass Production

Tablets containing Crystalline Forms 1 and 5 of the present invention were mass-produced (scale up) in order to confirm the similarity of dissolution pattern depending on crystalline forms in mass production. The dissolution test was performed for thus obtained tablets according to the same procedures as described above. Table 8 and FIG. 8 show the results.

TABLE 8

|  | 5 minutes | | 10 minutes | | 15 minutes | | 30 minutes | |
| --- | --- | --- | --- | --- | --- | --- | --- | --- |
|  | Mean | S.D. | Mean | S.D. | Mean | S.D. | Mean | S.D. |
| Tablets (Crystalline Form 1) | 55.2 | 7.2 | 86.7 | 2.3 | 92.5 | 1.9 | 97.3 | 0.5 |
| Tablets (Crystalline Form 5) | 55.2 | 1.9 | 82.1 | 2.3 | 91.8 | 0.8 | 97.5 | 2.2 |

Figure 8:
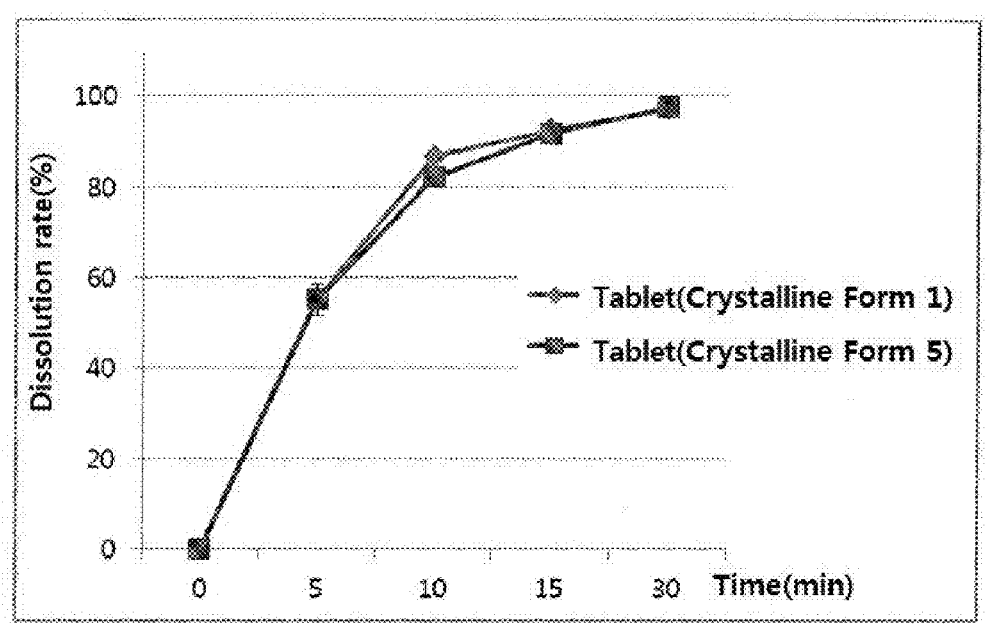
FIG. 8 is a graph showing the dissolution rates of tablets containing Crystalline Form 1 or 5 of the present invention depending on crystalline forms.

As shown in Table 8 and FIG. 8, the tablets containing Crystalline Forms 1 and 5 according to the present invention show decreased deviation in the dissolution pattern depending on crystalline forms, which confirms that the crystalline forms of the present invention have similar solubility and pharmacological effects in mass production.

While the invention has been described with respect to the above specific embodiments, it should be recognized that various modifications and changes may be made to the invention by those skilled in the art which also fall within the scope of the invention as defined by the appended claims.

The invention claimed is:

1. An anhydrous crystalline 5-chloro-N-({(5S)-2-oxo-3-[4-(5,6-dihydro-4H-[1,2,4]triazin-1-yl)phenyl]-1,3-oxazolidin-5-yl}methyl)thiophene-2-carboxamide methanesulfonate, whose X-ray powder diffraction spectrum using Cu-Kα radiation comprises peaks at an angle of diffraction 2θ of 12.022, 15.721, 15.971, 18.125, 18.928, 19.979, 20.311, 20.726, 21.66, 22.805, 23.18, 23.985, 25.857, 27.25, 27.829, 28, 28.189 and 29.753.

2. The anhydrous crystalline 5-chloro-N-({(5S)-2-oxo-3-[4-(5,6-dihydro-4H-[1,2,4]triazin-1-yl)phenyl]-1,3-oxazolidin-5-yl}methyl)thiophene-2-carboxamide methanesulfonate of claim 1, which shows a peak at 186±2° C. in a differential scanning calorimetry analysis.

3. A pharmaceutical composition comprising the anhydrous crystalline 5-chloro-N-({(5S)-2-oxo-3-[4-(5,6-dihydro-4H-[1,2,4]triazin-1-yl)phenyl]-1,3-oxazolidin-5-yl}methyl)thiophene-2-carboxamide methanesulfonate according to claim 1 and a pharmaceutically acceptable carrier or excipient.

4. A method for treating a disease or symptom selected from the group consisting of thrombosis, myocardial infarction, arteriosclerosis, inflammation, stroke, angina pectoris, recurrent stricture after angioplasty, and thromboembolism in a subject in need thereof, said method comprising administering the pharmaceutical composition of claim 3 to the subject.

* * * * *